United States Patent [19]
Reidmiller

[11] Patent Number: 5,843,062
[45] Date of Patent: Dec. 1, 1998

[54] CONTOURED NURSING PAD

[76] Inventor: Lora S. Reidmiller, 7104 Spruce Forest Ct., Tarrant County, Arlington, Tex. 76001

[21] Appl. No.: 697,983

[22] Filed: Sep. 4, 1996

[51] Int. Cl.$^6$ .............................. A61F 13/15; A61F 13/20
[52] U.S. Cl. ........................................ 604/378; 604/385.1
[58] Field of Search .................................. 604/378, 385.1, 604/368, 374, 392, 393, 397

[56] References Cited

U.S. PATENT DOCUMENTS

| | | | |
|---|---|---|---|
| D. 246,729 | 12/1977 | Murphy ..................................... | D24/49 |
| 2,748,771 | 6/1956 | Richards ................................... | 128/280 |
| 2,896,623 | 7/1959 | Ritzgerald ............................. | 604/385.1 |
| 3,442,268 | 5/1969 | Bird ........................................ | 128/280 |
| 3,502,083 | 3/1970 | Howard et al. ....................... | 604/385.1 |
| 3,738,362 | 6/1973 | Sneider .................................... | 128/280 |
| 4,047,534 | 9/1977 | Thomaschefsky et al. ............ | 128/461 |
| 4,074,721 | 2/1978 | Smits et al. .............................. | 128/461 |
| 4,125,114 | 11/1978 | Repke .................................... | 604/385.1 |
| 4,164,228 | 8/1979 | Weber-Unger ........................ | 604/385.1 |
| 4,193,404 | 3/1980 | Repke et al. .......................... | 604/385.1 |
| 4,674,510 | 6/1987 | Sneider .................................... | 128/481 |
| 4,875,492 | 10/1989 | Mitchell et al. ........................ | 604/378 |
| 5,017,174 | 5/1991 | Gowrylow ................................ | 450/37 |
| 5,149,336 | 9/1992 | Clarke et al. ......................... | 604/385.1 |
| 5,472,775 | 12/1995 | Obijeski et al. ........................ | 428/220 |

*Primary Examiner*—John G. Weiss
*Assistant Examiner*—Ki Yong O
*Attorney, Agent, or Firm*—Lisa L.B. Yociss

[57] ABSTRACT

A contoured nursing pad for absorbing fluid from a woman's breast including a first layer having a top, a second layer having a top, bottom, and middle, a third, annular layer having an aperture, top, and bottom, and a fourth layer having a bottom. The bottom of the second layer is secured to the top of the first layer. The bottom of the third layer is secured to both the top of the first layer and the top of the second layer. The middle of the second layer is received within the aperture of the third layer. The bottom of the fourth layer is secured to the top of the third layer and the top of the second layer.

In accordance with a preferred embodiment, the first layer includes a first area and a second area. The second area of the first layer includes a first plurality of non-uniform gathers. The fourth layer includes a first area and a second area. The second area of the fourth layer includes a second plurality of non-uniform gathers. The first areas of the first and fourth layers do not include any gathers.

The pad includes a circumference and a radius. The third layer is capable of expanding or contracting in any direction. The first and second plurality of gathers permit the pad to expand or contract only in a circumferential direction. The gathers are shaped so as to permit only a part of the pad to expand or contract while the remainder of the pad retains its original shape. The circumference of the pad expands or contracts while the radius of the pad remains constant.

8 Claims, 4 Drawing Sheets

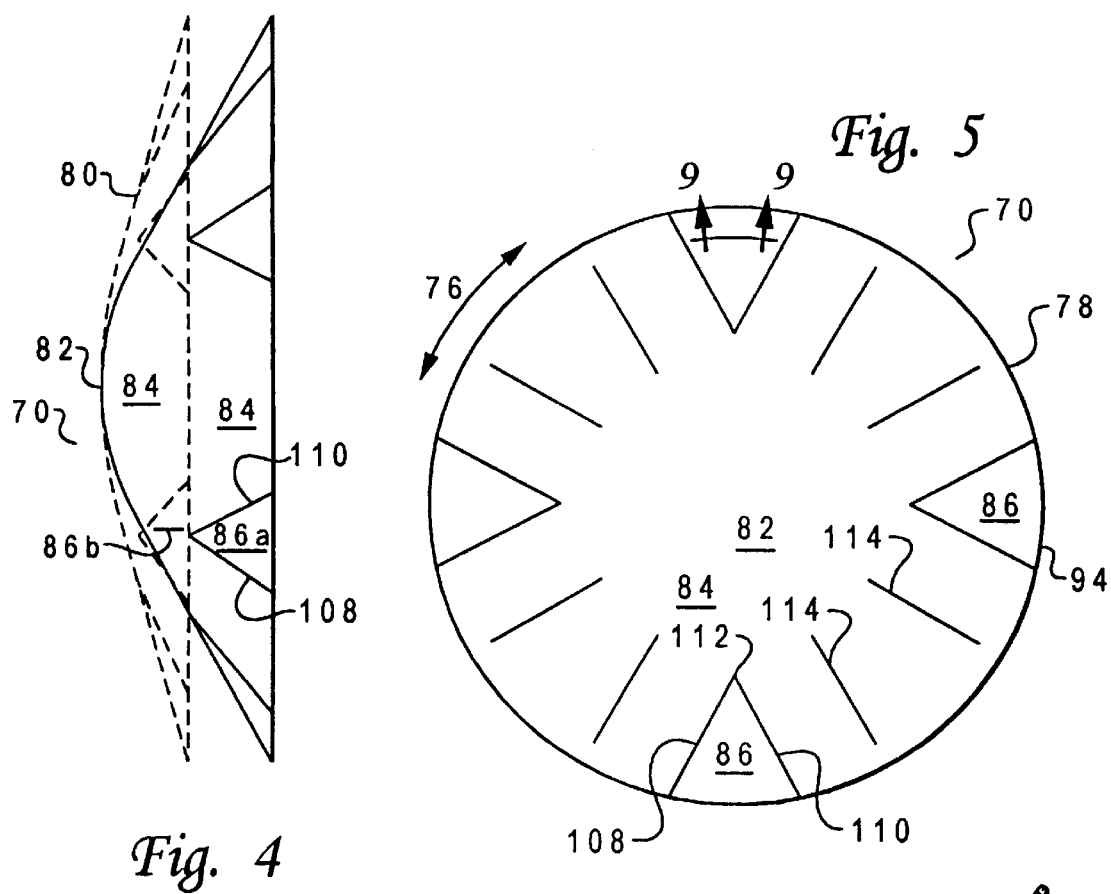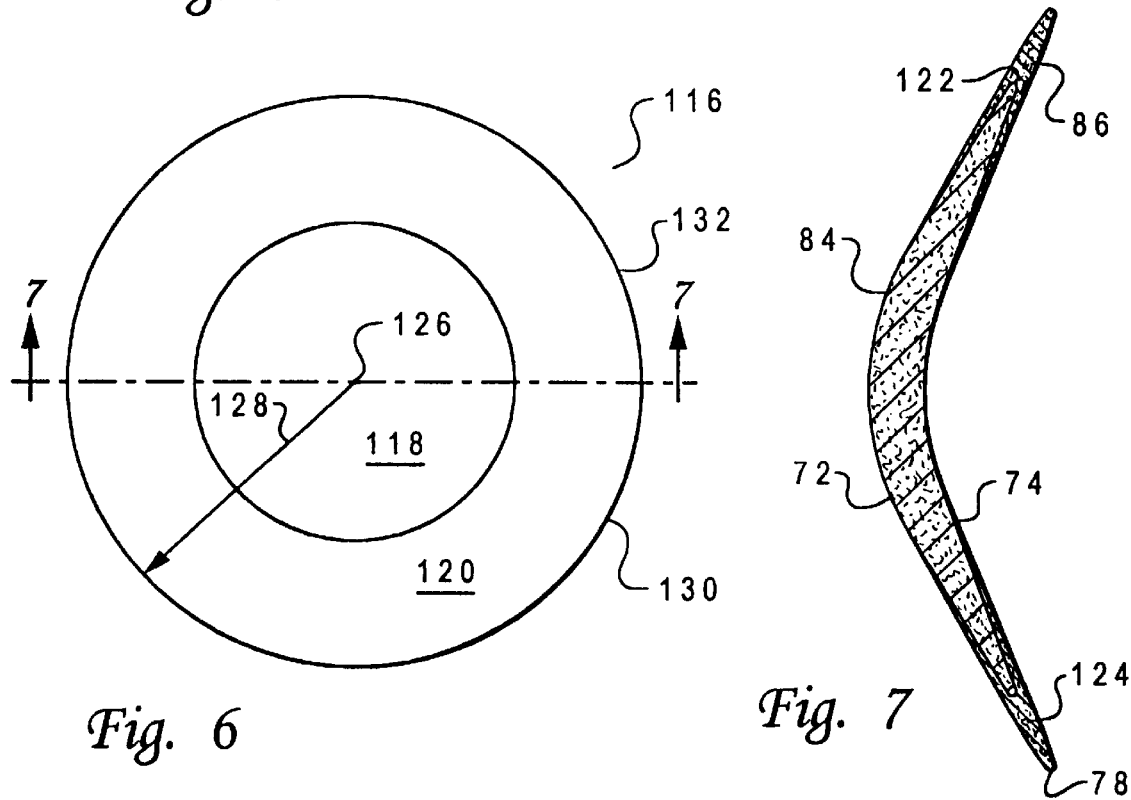

CONTOURED NURSING PAD

BACKGROUND OF THE INVENTION

1. Technical Field

The present invention relates to a contoured pad for absorbing fluid from a woman's breast, and in particular to a contoured pad for absorbing fluid from a woman's breast including a first layer including a middle, and an annular layer which includes an aperture so that the middle of the first layer is received within the aperture of the annular layer. Still more particularly, the present invention relates to a contoured pad for absorbing fluid from a woman's breast including a first layer including a middle, and an annular layer which includes an aperture so that the middle of the first layer is received within the aperture of the annular layer, where the annular layer is capable of automatically expanding or contracting, so that the pad will continuously adapt to the breast size during breast enlargement or shrinkage by automatically expanding or contracting.

2. Description of the Related Art

During lactation, it is common for breast milk to periodically leak from a woman's breasts. To prevent the milk from saturating the woman's clothing, many women utilize pads which absorb the milk which are called nursing pads.

Nursing pads are well known in the art. The pads are typically formed from multiple layers and may be either flat or shaped, such as conical shaped. The conical-shaped pads include an apex which is very pointed and may be uncomfortable and observed through the clothing. Other known pads are very bulky and flat, and do not change their shape when utilized. All of the known pads, including those that are shaped, do not fit snugly against the woman's body when used. As a result, breast milk leaks through the woman's clothing or onto bed linens during sleep. Not only does this leakage require additional cleanup for a nursing mother, but it can also create embarrassment when leaks appear through outer garments. Another problem of known pads is puckering due to a non-conforming pad and an outline which can been seen through the clothing also causing embarrassment.

It is common during lactation for a woman's breast size and shape to change. The breast may be fuller during times just before feeding an infant, and may be smaller after feedings. The known nursing pads do not easily adapt to the shape the breast may be. Although some of the pads are contoured and shaped prior to use, the pads retain their original shape during use regardless of the changing shape and size of the woman's breast, thus exacerbating the problems described above. Although a woman may have selected a pad which is close to her breast size, during lactation it is very likely that the pad can be both significantly too big and too small through the course of a typical day.

Further, most prior art pads are not formed to fit a typical woman's breast. For example, the pads are not shaped to accommodate a breast which is fuller on the bottom than on the top. The nursing mother's breast shape may change in a non-uniform manner during the course of a day. The breast may become fuller prior to feedings primarily on the bottom of the breast and less full on the top.

Known pads do not permit a pad to continuously change its shape according to the current shape of the woman's breast. In addition, known pads do not permit the pad to expand and contract selectively in only a portion of the pad.

One known pad describes a process of making a pad to permit the pad to stretch. U.S. Pat. No. 4,193,404, issued to Repke et al., describes micropleating either one or all of the layers of the pad. This permits the pad to stretch radially outward from the center of the pad along only one axis of the pad. This pad will not stretch along its transverse axis, or in any direction other than along the one axis.

SUMMARY OF THE INVENTION

A contoured nursing pad for absorbing fluid from a woman's breast including a first layer having a top, a second layer having a top, bottom, and middle, a third, annular layer having an aperture, top, and bottom, and a fourth layer having a bottom. The bottom of the second layer is secured to the top of the first layer. The bottom of the third layer is secured to both the top of the first layer and the top of the second layer. The middle of the second layer is received within the aperture of the third layer. The bottom of the fourth layer is secured to the top of the third layer and the top of the second layer.

In accordance with a preferred embodiment, the first layer includes a first area and a second area. The second area of the first layer includes a first plurality of non-uniform gathers. The fourth layer includes a first area and a second area. The second area of the fourth layer includes a second plurality of non-uniform gathers. The first areas of the first and fourth layers do not include any gathers.

The pad includes a circumference and a radius. The third layer is capable of expanding or contracting in any direction. The first and second plurality of gathers permit the pad to expand or contract only in a circumferential direction. The gathers permit only a part of the pad to expand or contract while the remainder of the pad retains its relaxed position. The circumference of the pad expands or contracts while the radius of the pad remains constant.

The above as well as additional objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

FIG. 4 is a side view of a second embodiment of a contoured pad depicting the pad contracted, and depicting in phantom the pad expanded in accordance with the present invention;

FIG. 5 is a top view of the second embodiment of a contoured pad having a first portion and a plurality of second portions and channels in accordance with the present invention;

FIG. 6 is a top view of a third embodiment of a contoured pad having a first portion and a second portion in accordance with the present invention;

FIG. 7 is a cross-sectional view taken along line 7—7 shown in FIG. 6 in accordance with the present invention;

DETAILED DESCRIPTION OF PREFERRED EMBODIMENT

Figure 1A:
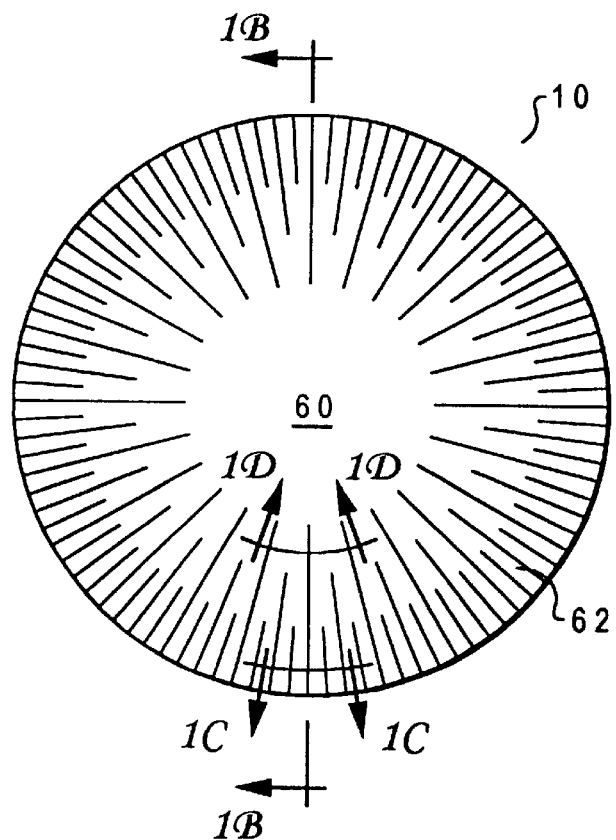
FIG. 1A is a top view of a contoured pad in accordance with the present invention.

During lactation, it is common for breast milk to periodically leak from a woman's breasts. To prevent the milk from saturating the woman's clothing, many women utilize pads which absorb the milk which are called nursing pads.

It is also common during lactation for a woman's breast size and shape to change. The breast may be fuller during times just before feeding an infant, and may be smaller after feedings. The known nursing pads do not continuously adapt to the shape the breast may be. Although some of the pads are contoured and shaped, the pads retain their original shape regardless of the current shape and size of the woman's breast. Although a woman may have selected a pad which is close to her breast size, during lactation it is very likely that the pad can be both significantly too big and too small through the course of a typical day.

A need exists for a nursing pad which is comfortable as well as absorbent. The present invention is a pad which is contoured and shaped to fit a woman's breast. Further, the pad will continuously expand and contract to continuously adapt to the current size of the woman's breast. The pad is formed to be mostly absorbent at its center and mostly stretchable at its perimeter. The pad has a generally convex surface which will fit against the woman's clothing and a concave surface for fitting against the woman's skin. A first embodiment of the pad includes multiple layers where a third layer is annular having an aperture through the middle. A middle of a second layer which is absorbent is received within the aperture. A first layer is moisture permeable and is received against a woman's skin. A fourth layer is moisture impermeable and is received within a woman's clothing. The third layer is stretchable.

The first layer includes a first area and a second area. The first and second areas of the first layer are formed integrally together so that the second area is formed annularly around the first layer. The second area of the first layer includes a first plurality of non-uniform gathers. The fourth layer includes a first area and a second area. The first and second areas of the fourth layer are formed integrally together so that the second area is formed annularly around the first layer. The second area of the fourth layer includes a second plurality of non-uniform gathers. The first areas of the first and fourth layers do not include any gathers. The first and second pluralities of gathers are generally larger toward a perimeter of the pad and gradually become smaller toward the first areas of the first and fourth layers.

The pad includes a circumference and a radius. The third layer is capable of expanding or contracting in any direction. The first and second pluralities of gathers permit the pad to expand or contract only in a circumferential direction. The gathers permit only a portion of the pad to expand or contract while the remainder of the pad retains its relaxed position. For example, a lower portion of the pad may expand while an upper portion of the pad is contracting. The circumference of the pad may expand or contract while the radius of the pad remains constant.

A second and a third embodiment of the pad include a first portion which is absorbent and at least one second portion. The second portion will expand and contract in a circumferential direction. The second portion will not expand or contract in a radial direction outward from the center of the pad. By expanding and contracting in a circumferential direction only, the pad will automatically change its shape to fit the current size of the woman's breast.

Figure 1B:
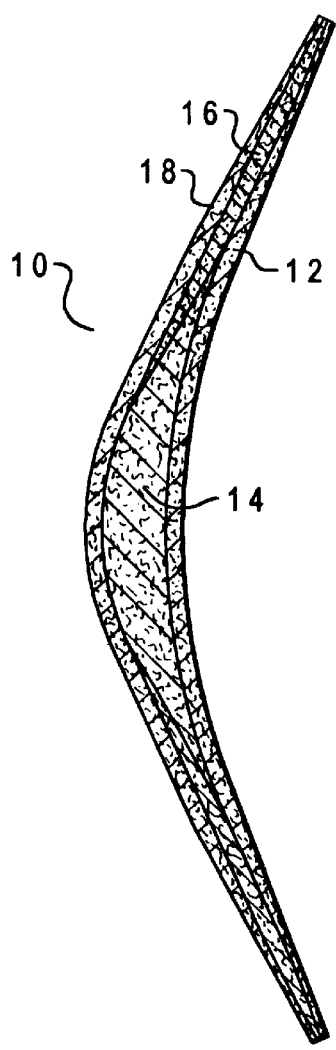
FIG. 1B is a cross-sectional view of the contoured pad of FIG. 1A taken along line 1B—1B, depicting multiple layers in accordance with the present invention.
Figure 2:
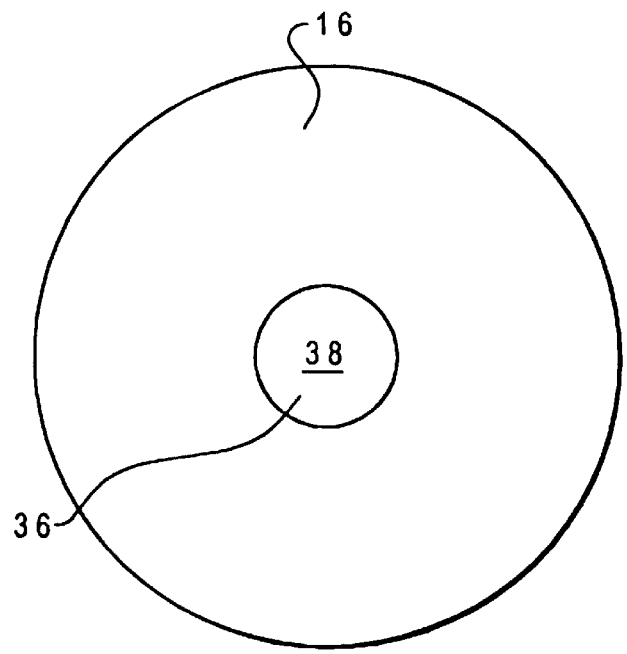
FIG. 2 is a top view of a third, annular layer in accordance with the present invention.
Figure 1C:
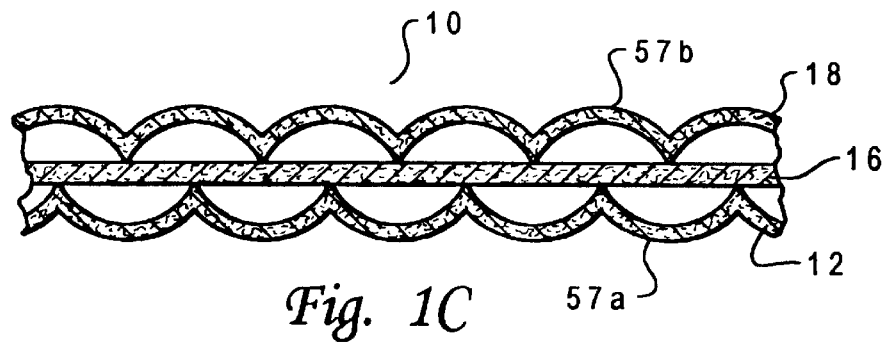
FIG. 1C is a cross-sectional view of the pad of FIG. 1A taken along line 1C—1C depicting a first and a second plurality of gathers in accordance with the present invention.
Figure 1D:
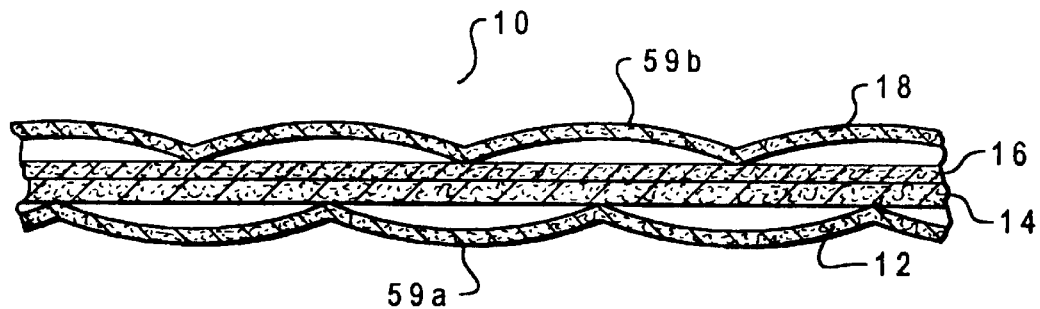
FIG. 1D is a cross-sectional view of the pad of FIG. 1A taken along line 1D—1D depicting a first and a second plurality of gathers in accordance with the present invention.
Figure 3:
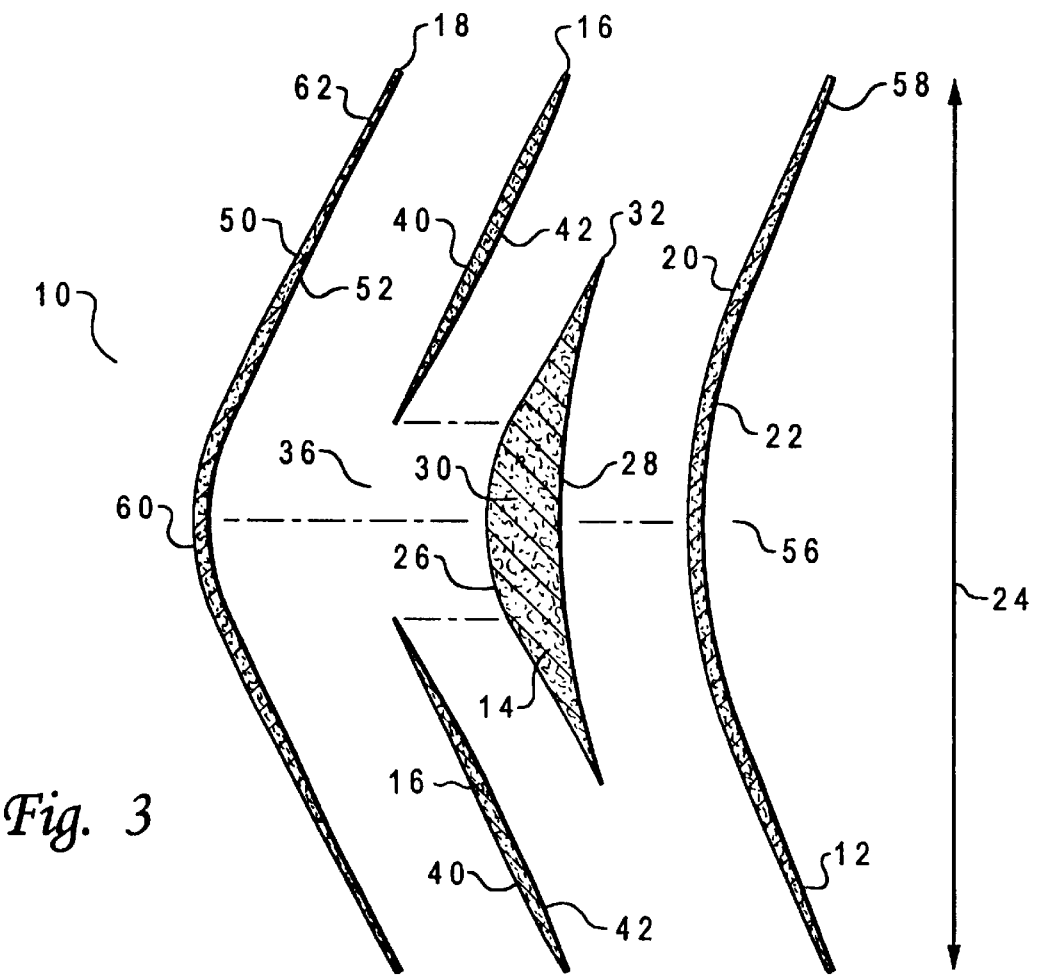
FIG. 3 is an exploded cross-sectional view of the pad of FIG. 1B taken along line 1B—1B in accordance with the present invention.
Figure 8:
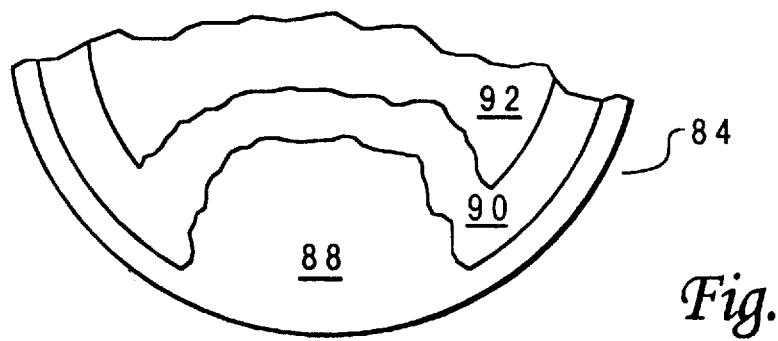
FIG. 8 is a partial perspective view of a first portion of either the second or third embodiments of a contoured pad having multiple layers in accordance with the present invention.
Figure 9:
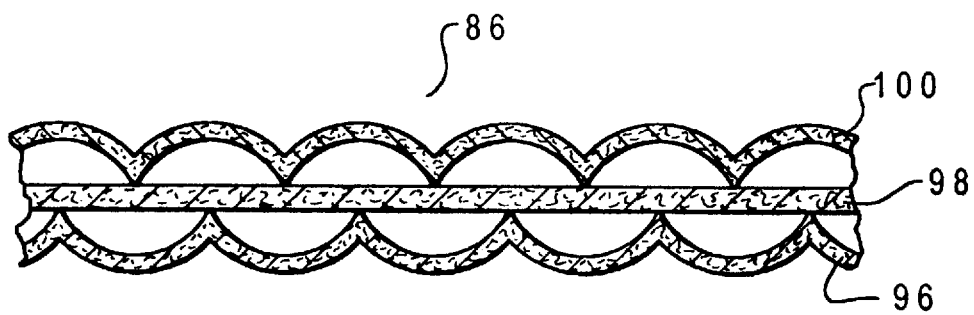
FIG. 9 is a partial cross-sectional view of a second embodiment of the second portion taken along line 9—9 shown in FIG. 5, where the second embodiment of the second portion includes multiple layers in accordance with the present invention.

Referring now to the figures, FIG. 1A is a top view of a contoured pad in accordance with the present invention. FIG. 1B is a cross-sectional view of the contoured pad of FIG. 1A taken along line 1B—1B, depicting multiple layers in accordance with the present invention. FIG. 1C is a cross-sectional view of the pad of FIG. 1A taken along line 1C—1C depicting a first and a second plurality of gathers in accordance with the present invention. FIG. 1D is a cross-sectional view of the pad of FIG. 1A taken along line 1D—1D depicting a first and a second plurality of gathers in accordance with the present invention. FIG. 2 is a top view of a third, annular layer in accordance with the present invention. FIG. 3 is an exploded cross-sectional view of the pad of FIG. 1B taken along line 1B—1B in accordance with the present invention. FIG. 4 is a side view of a second embodiment of a contoured pad depicting the pad contracted, and depicting in phantom the pad expanded in accordance with the present invention. FIG. 5 is a top view of the second embodiment of a contoured pad having a first portion and a plurality of second portions and channels in accordance with the present invention. FIG. 6 is a top view of a third embodiment of a contoured pad having a first portion and a second portion in accordance with the present invention. FIG. 7 is a cross-sectional view taken along line 7—7 shown in FIG. 6 in accordance with the present invention. FIG. 8 is a partial perspective view of a first portion of either the second or third embodiments of a contoured pad having multiple layers in accordance with the present invention. FIG. 9 is a partial cross-sectional view of a second embodiment of the second portion taken along either line 9—9 shown in FIG. 5, where the second embodiment of the second portion includes multiple layers in accordance with the present invention.

A contoured pad 10 may be used by lactating women to absorb fluid from the woman's breast. Pad 10 is preferably disposable but may be reusable. Pad 10 is contoured to be shaped generally like a woman's breast.

Pad 10 includes a first 12, a second 14, a third 16, and a fourth layer 18 which are preferably thermally bonded together. Those skilled in the art will recognize that any suitable method of securing the layers together may be utilized. First layer 12 is moisture permeable. First layer 12 is preferably formed from a non-woven fabric sheet, such as disclosed in U.S. Pat. No. 4,892,532, which is incorporated herein by reference. First layer 12 is contoured and includes a top 20 and a bottom 22, and has a diameter. Bottom 22 of first layer 12 is received against a woman's breast.

Second layer 14 is contoured and includes a top 26, a bottom 28, a middle 30, a perimeter 32, and has a diameter.

Second layer 14 is absorbent. Second layer is preferably formed by treating loose fibers with a gelling agent where the number of fibers is greater in the middle of the second layer and lower at the perimeter of the layer. One type of fibers which may be utilized to form second layer 14 are copolymer micro-fibers, such as disclosed in U.S. Pat. No. 4,923,454 which is incorporated herein by reference. One type of gelling agent which may be utilized is described in U.S. Pat. No. 4,935,022 which is incorporated herein by reference. Middle 30 of second layer 14 is more absorbent than perimeter 32 of second layer 14. Bottom 28 of second layer 14 is secured to a portion of top 20 of first layer 12.

Third layer 16 is annular. Third layer 16 includes an aperture 36 through generally a middle 38 of third layer 16. Third layer 16 also includes a top 40, a bottom 42, and a diameter. Third layer 16 is capable of expanding or contracting. Third layer 16 is formed from a non-woven fabric sheet made from elasticized fiber strands. A first portion of bottom 42 of third layer 16 is secured to a portion of top 20 of first layer 12 and a second portion, the remainder, of bottom 42 is secured to top 26 of second layer 14, so that middle 30 of second layer 14 is received within aperture 36. Therefore, bottom 42 is secured to either a portion of top 26, or a portion of top 20.

Fourth layer 18 is moisture impermeable and includes a top 50, a bottom 52, and a diameter. Top 50 of fourth layer 18 is received against a woman's clothing. A first portion of bottom 52 of fourth layer 18 is secured to top 40 of third layer 16, a second portion, the remainder, of bottom 52 is secured to top 26 of second layer 14. Fourth layer 18 is a web of non-woven fibers which are preferably treated with a laminating material which will make the layer moisture impermeable, such as by treating fourth layer 18 with a light plastic or rubber latex.

First layer 12 includes a first area 56, and a second area 58 formed integrally around first area 56. Second area 58 of first layer 12 includes a first plurality of non-uniform gathers. First area 56 does not include any gathers. The first plurality of non-uniform gathers are shaped and spaced so that multiple gathers located near the perimeter of the pad are larger and spaced closer together to permit greatest stretching, as depicted by multiple gathers 57a shown in FIG. 1C. Multiple gathers located near the first area 56 are smaller and spaced farther apart to permit only slight stretching, as depicted by multiple gathers 59a shown in FIG. 1D. The plurality of gathers are shaped and spaced so that the gathers gradually become smaller and spaced farther apart as the gathers near the first area 56.

Similarly, fourth layer 18 includes a first area 60, and a second area 62 formed integrally around first area 60. Second area 62 of fourth layer 18 includes a second plurality of gathers. The second plurality of non-uniform gathers are shaped and spaced so that multiple gathers located near the perimeter of the pad are larger and spaced closer together to permit greatest stretching, as depicted by multiple gathers 57b shown in FIG. 1C. Multiple gathers located near the first area 60 are smaller and spaced farther apart to permit only slight stretching, as depicted by multiple gathers 59b shown in FIG. 1D. The plurality of gathers are shaped and spaced so that the gathers gradually become smaller and spaced farther apart as the gathers near the first area 60.

Second area 58 of first layer 12 and second area 62 of fourth layer 18 are stretchable because they are gathered as depicted in FIGS. 1A, 1B, 1C, and 1D. Because of the non-uniform shape and spacing of the first and second plurality of gathers, the pad will continuously adapt its shape to conform to the shape of the woman's breast. Therefore, the pad will not always be uniformly and symmetrically shaped when worn. If the shape of the woman's breast changes during use of the pad, the pad will then adapt its shape.

Diameters of first, third, and fourth layers are generally equal as depicted at reference number 24. In a preferred embodiment, diameters are approximately five (5) inches. Diameter of second layer is preferably four (4) inches. Aperture 36 is preferably located generally in middle 38 of third layer 16, and is approximately two (2) inches in diameter.

In a second embodiment, multiple second portions are utilized, as illustrated in FIGS. 4 and 5. These portions are generally triangular shaped and are placed symmetrically around the pad. Each of these second portions are separated from each other by the first portion. This embodiment will also permit the pad to expand non-uniformly. If the lower area of the breast becomes fuller, only the lower area of the pad will expand. Therefore, the pad will not always be uniformly and symmetrically shaped.

Pad 70 includes a convex outer surface 72 and a concave inner surface 74. Outer surface 72 may be received within a bra and contacts the woman's clothing. Inner surface 74 rests against the woman's skin.

Pad 70 includes a perimeter 78 of the pad and a radius 80 from a center 82 of pad 70 to perimeter 78. Radius 80 will be a constant length from center 82 to any point along perimeter 78. Pad 70 is preferably thicker in its middle near center 82 and becomes thinner nearing perimeter 78 of pad 70.

Pad 70 includes a first portion 84 and at least one second portion 86. The embodiment illustrated in FIG. 5 includes four separate second portions 86. The third embodiment, illustrated in FIG. 6, includes pad 116 having one second portion 120. Those skilled in the art will understand that any number of second portions may be utilized.

First portion 84 is absorbent. First portion 84 may be formed from multiple layers as depicted in FIG. 8. A first layer 88 is moisture permeable but non-wettable. First layer 88 is preferably formed similarly to first layer 12. A second layer 90 is absorbent and preferably formed similarly to second layer 14. A third layer 92 is a moisture impermeable layer for preventing fluid from striking through onto clothing. Third layer 92 is preferably formed similarly to fourth layer 18.

Second portion 86 is formed from a stretchable material which will permit stretching in the circumferential direction of pad 70 only. Second portion 86 includes an arc 94 which is coincident with perimeter 78 of pad 70. In the embodiment shown in FIG. 5, each second portion 86 includes an arc 94 which is comprised by perimeter 78. In the embodiment shown in FIG. 6, second portion 120 includes a single arc 130 which is coincident with perimeter 132 of pad 116.

Second portions 86 or 120 include at least one layer, and may include multiple layers formed from different materials. For example, shown in FIG. 9, second portion 86 will include a first layer 96, a second layer 98, and a third layer 100.

Referring to FIGS. 4 and 5, an embodiment is illustrated which includes multiple second portions 86. Each of the second portions 86, are generally triangular shaped whereby arc 94 is included within perimeter 78. Second portions 86 each include two sides 108 and 110. The triangle includes an apex 112. One end of each side 108 and 110 meet to form apex 112. Apex 112 may be located at any point within pad 70 but is preferably located between center 82 and perimeter 78. Second portions 86 are preferably spaced symmetrically around pad 70. Second portions 86 may be secured to pad 70 by any suitable method, such as by thermal bonding.

Pad 70 depicted in FIG. 5 may include channels 114. Channels 114 extend from near center 82 to near perimeter 78. Channels 114 have a high capillarity to permit fluid to flow away from center 82 toward perimeter 78. Those skilled in the art will recognize that channels 114 may be included any embodiment, such as the embodiment depicted in FIGS. 1A–1D, and FIG. 6.

The embodiment of pad 116 depicted in FIG. 6, includes a perimeter 132 of pad 116, a radius 128 from a center 126 to perimeter 132. Pad 116 includes only one second portion 120. Second portion 120 is annular and is located generally at a perimeter 122 of first portion 118. Second portion 120 preferably receives perimeter 122 of first portion 118 within second portion 120 so that second portion 120 envelopes perimeter 122. In this manner, fluid may be drawn from first portion 118 and into a reservoir 124 created by second portion 120 as shown in FIG. 7.

All embodiments of the pads offer many advantages over the prior art. The pad is contoured to be shaped more like a woman's breast than the prior art pads, such as the conical pads. The pad may be manufactured in different sizes and colors to better suit a particular woman's typical size and individual preferences.

Pad 10 is formed from multiple layers. A second layer is very absorbent and is received with the aperture of the third layer. The third layer is stretchable. In this manner, pad 10 permits moisture to be wicked through a first layer and into the second layer which will retain the moisture. The fourth layer is moisture impermeable so that the moisture does not strike through onto a woman's clothing. The third layer permits the pad to stretch so that the pad will continue to conform to the woman's breast size and shape as the breast size and shape change throughout the time the pad is being worn. The first and second plurality of gathers permit the pad to continuously adapt its shape.

Pads 70 and 116 each include two portions, a first absorbent portion and a second expandable and contractible portion. The second portion is secured to the first portion in order to permit the pad to automatically adjust to the breast size and shape of a woman without the need for the woman to utilize a different sized or shaped pad. The second portion permits expansion and contraction in a circumferential direction 76 about the center of the pad. The second portion does not expand or contract in the radial direction. Thus the perimeter 78 of pad 70 will expand or contract, respectively, permitting the pad to continuously adapt to the breast size.

The result of the expansion and contraction is illustrated in FIG. 4. When the breast is fuller, second portions 86a are expanded causing perimeter 78, shown in FIG. 5, to become larger. Radius 80 is constant. When the breast is smaller, second portions 86b are contracted causing perimeter 78 to become smaller. Radius 80 remains the same. First portion 84 does not expand or contract during this process.

In addition, the placement of the second portions permit the pad to expand and contract in a non-uniform fashion. For example, if during lactation the bottom portion of a woman's breast becomes fuller, the bottom of the pad will expand while the top remains the same.

While the invention has been particularly shown and described with reference to a preferred embodiment, it will be understood by those skilled in the art that various changes in form and detail may be made therein without departing from the spirit and scope of the invention.

What is claimed is:

1. A contoured pad for absorbing fluid from a woman's breast, comprising:
    a first contoured layer having a top;
    a second contoured layer having a top and a bottom and including a middle, said bottom of said second layer secured to said top of said first layer;
    a third contoured, annular layer having an aperture through generally a middle of said third layer, a top, and a bottom, said bottom of said third layer secured to said top of said first layer and to said top of said second layer, wherein said middle of a second portion is received within said aperture; and
    a fourth layer having a bottom, said bottom of said fourth layer secured to said top of said third layer and to said top of said second layer.

2. The pad according to claim 1, wherein said first layer further includes a first area and a second area formed integrally with said first area of said first layer, said second area of said first layer being stretchable; and wherein said fourth layer further includes a first area and a second area formed integrally with said first area of said fourth layer, said second area of said fourth layer being stretchable.

3. The pad according to claim 1, further comprising said first layer including a bottom which is capable of being received by a woman's breast.

4. The pad according to claim 1, further comprising said first layer being moisture permeable, said middle of said second layer being absorbent, and said fourth layer being moisture impermeable.

5. The pad according to claim 1 wherein said pad further includes a perimeter and a surface radial length, further comprising said third layer being capable of expanding or contracting so that said perimeter of said pad expands or contracts while said surface radial length of said pad remains constant, whereby said pad is capable of expanding or contracting only in a circumferential direction.

6. The pad according to claim 1, wherein said first, third, and fourth layers each includes a diameter, and said diameter of said first layer is equal to said diameter of said third layer and said diameter of said fourth layer.

7. The pad according to claim 1 further comprising:
    said first layer including a center, a perimeter, a first area, and a second area, wherein said first area is located near said center and said second area is located near said perimeter; and
    said second area of said first layer including a first plurality of non-uniform gathers, said first plurality of gathers being larger near said perimeter and smaller near said center.

8. The pad according to claim 7 further comprising:
    said fourth layer including a center, a perimeter, a first area, and a second area, wherein said first area is located near said center and said second area is located near said perimeter; and
    said second area of said second layer including a second plurality of non-uniform gathers, said second plurality of gathers being larger near said perimeter and smaller near said center.

* * * * *